US00PP26696P3

(12) United States Plant Patent
Scheffers

(10) Patent No.: US PP26,696 P3
(45) Date of Patent: May 3, 2016

(54) ***DRACAENA* PLANT NAMED 'DRAWHIGRE'**

(50) Latin Name: *Dracaena fragrans*
Varietal Denomination: DRAWHIGRE

(71) Applicant: Ruud Scheffers, Honselersdijk (NL)

(72) Inventor: Ruud Scheffers, Honselersdijk (NL)

(73) Assignee: Dragontree Beheer B.V. (NL)

( * ) Notice: Subject to any disclaimer, the term of this patent is extended or adjusted under 35 U.S.C. 154(b) by 122 days.

(21) Appl. No.: 14/120,542

(22) Filed: Jun. 2, 2014

(65) Prior Publication Data

US 2015/0351303 P1 Dec. 3, 2015

(51) Int. Cl.
*A01H 5/00* (2006.01)

(52) U.S. Cl.
USPC ..... Plt./383

(58) Field of Classification Search
USPC ..... Plt./383
See application file for complete search history.

*Primary Examiner* — Annette Para
(74) *Attorney, Agent, or Firm* — Cassandra Bright

(57) ABSTRACT

A new and distinct *Dracaena* cultivar named 'DRAWHIGRE' is disclosed, characterized by Unique dark green, greyed-green and white foliage. Plants grow in a distinctive upright habit. The new variety is a *Dracaena*, typically produced as an ornamental plant.

1 Drawing Sheet

Latin name of the genus and species: *Dracaena fragrans*.
Variety denomination: 'DRAWHIGRE'.

BACKGROUND OF THE INVENTION

The new cultivar is the product of chance discovery. The new variety originated as a naturally occurring branch mutation of the variety *Dracaena fragrans* 'Malaika'.

The new variety was discovered by the inventor, Ruud A. M. Scheffers, a citizen of the Netherlands, in 2010 in a commercial greenhouse belonging to the inventor in Honselersdijk, the Netherlands. After identifying the new variety as a potentially interesting selection, the inventor continued confidential testing and propagation of 'DRAWHIGRE' assessing stability of the unique characteristics of this variety.

Asexual reproduction of the new cultivar 'DRAWHIGRE' was first performed at the commercial greenhouse in Honselersdijk, the Netherlands by vegetative cuttings in 2010. Access to all plants was restricted, as plants were kept in a locked greenhouse not open to the public. Through subsequent propagation by vegetative cuttings, multiple generations have been reproduced, which have shown that the unique features of this cultivar are stable and reproduced true to type. Plants were first made available to the public in the Netherlands Nov. 1, 2013.

SUMMARY OF THE INVENTION

The cultivar 'DRAWHIGRE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DRAWHIGRE'. These characteristics in combination distinguish 'DRAWHIGRE' as a new and distinct *Dracaena* cultivar:

1. Unique dark green, greyed-green and white foliage.
2. Upright growth.

PARENT COMPARISON

Plants of the new cultivar 'DRAWHIGRE' are similar to the parent, *Dracaena fragrans* 'Malaika' in most horticultural characteristics. The new variety, however, differs in the following:

1. The new variety produces foliage which is dark green, greyed-green with a broad white stripe. The parent variety produces foliage which is yellow-green, and green with thin, white striping.
2. Plants of the parent variety are more compact.
3. Plants of the parent variety are shorter, and produce leaves with more twisting.

COMMERCIAL COMPARISON

'DRAWHIGRE' can be compared to the unpatented commercial variety *Dracaena fragrans* '2004030D', U.S. Plant Pat. No. 24,148. The varieties are similar in most horticultural characteristics, however, 'DRAWHIGRE' differs from '2004030D' in the following:

1. The new variety has shorter leaves.
2. The new variety produces leaves which are more upright.
3. The new variety produces more leaves.
4. The distribution of color/striping of the leaves is different, although the colors are similar.

BRIEF DESCRIPTION OF THE PHOTOGRAPH

The accompanying photograph in FIG. 1 illustrates in full color a typical plant of 'DRAWHIGRE' grown in a commercial greenhouse in Honselersdijk, the Netherlands. This plant is approximately 4 months old, shown planted in a 19 cm container.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'DRAWHIGRE' plants grown in a greenhouse in Honselersdijk, The Netherlands. A steady temperature of approximately 20° C. at night and 20° C. during the day was maintained. No artificial light, photoperiodic treatments were given to the plants. Measurements and numerical values represent averages of typical plant types.

Botanical classification: *Dracaena fragrans* 'DRAWHIGRE'.

PROPAGATION

Time to initiate rooting: About 5 to 6 weeks at approximately 20° C. 6 weeks for full rooting.

Root description: Moderately thick, moderately fibrous, not fleshy, coloured greyed-orange; near RHS 174C and 174D.

PLANT

Age of plant described: 4 months.

Pot size of plant described: 19 cm pot.

Growth habit: Upright.

Height: Approximately 48.0 cm.

Plant spread: Approximately 61.2 cm.

Growth rate: Moderate, approximately 10 cm per month.

Branching characteristics: Not free branching, typically growing with one main stem from the base. Will only develop lateral branches after pinching/pruning.

Diameter of stem: Approximately 1.8 cm.

Internode length: Average 0.8 cm.

Texture of stem: Smooth, slightly glossy.

Color of stem: Green; near RHS 137B, marbled white; near RHS 155D and NN155A.

Stem strength: Very strong.

Number of leaves per stem: Average 40.

FOLIAGE

Leaf:

*Arrangement.*—Alternate (spirally).

*Average length.*—Approximately 36.7 cm.

*Average width.*—Approximately 5.1 cm.

*Shape of blade.*—Lorate.

*Aspect.*—Leaves in an average angle of 45° to main stem (=0°), tips curved downward in an average angle of 45° to horizontal (=0°).

*Apex.*—Acuminate.

*Base.*—Broad cuneate.

*Attachment.*—Sheathing.

*Margin.*—Entire, slightly undulate.

*Texture of top surface.*—Smooth, glossy.

*Texture of bottom surface.*—Smooth, glossy.

*Color.*—Young foliage upper side: Green; near RHS N137A, with a greyed-green central band; near RHS 189A and 190A, central band margined and striped white; near NN155C. Young foliage under side: Green; in between near RHS 137A and N137B, with a greyed-green central band; near RHS 189B and 191B, margined and striped white; near NN 155C. Mature foliage upper side: Green to yellow-green; in between near RHS N137A and 147A but darker, with a greyed-green central band; near RHS 189A, central band margined and striped white; near 155B. Mature foliage under side: Green to yellow-green; in between near RHS N137A and 146A, with a greyed-green central band; near RHS 189B and N189B, margined and striped white; near 155B.

*Venation.*—Type: parallel. Color: Upperside: Indistinguishable from leaf blade. Underside: Green; near RHS 137B to 137C.

Sheath:

*Average length.*—Approximately 2.4 cm.

*Average width.*—Approximately 5.4 cm (folded open).

*Color.*—Green-white; near RHS 157A, margined white; near RHS NN155C.

*Texture.*—Smooth, slightly glossy.

OTHER CHARACTERISTICS

Flower production: Not observed.

Disease resistance: Neither resistance nor susceptibility to normal diseases and pests of *Dracaena* has been observed.

Drought tolerance and temperature tolerance: Moderately high drought resistance, good heat resistance.

Fruit/seed production: Not observed.

What is claimed is:

1. A new and distinct cultivar of *Dracaena* plant named 'DRAWHIGRE' as herein illustrated and described.

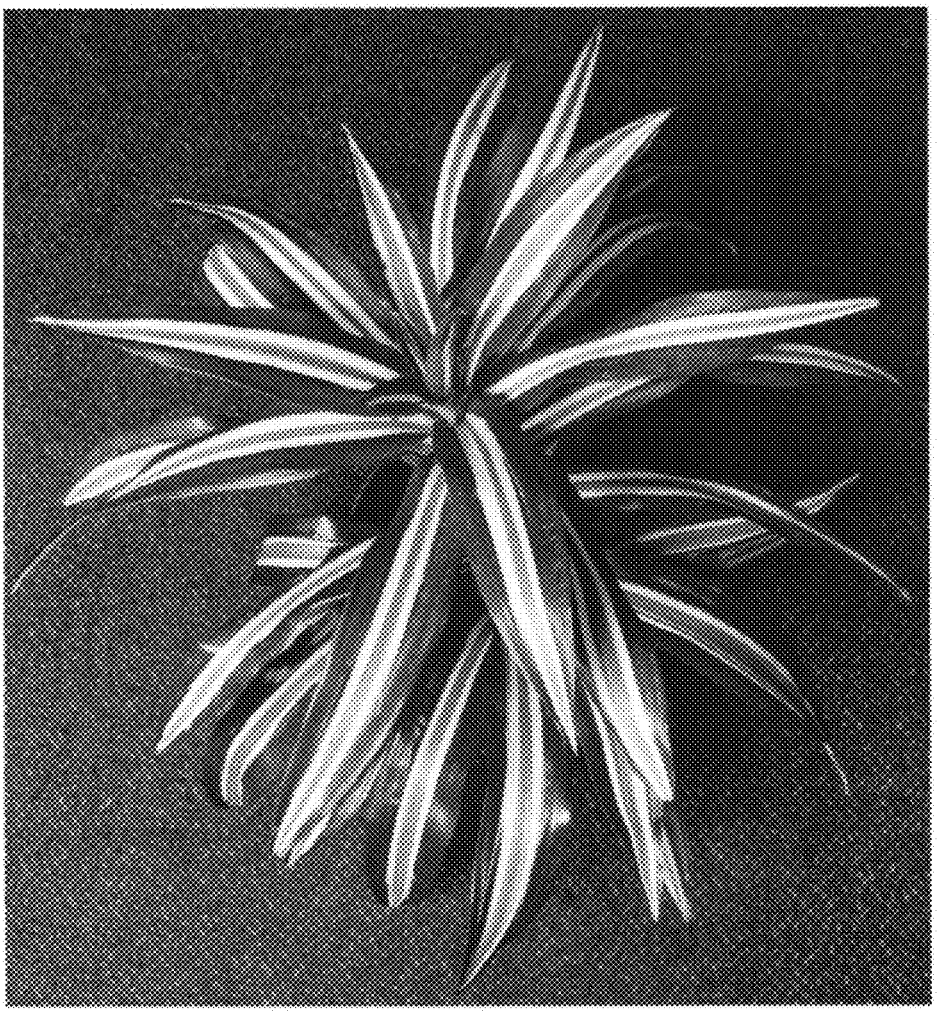

* * * * *